(12) United States Patent
Vandenburg

(10) Patent No.: US 10,279,187 B2
(45) Date of Patent: May 7, 2019

(54) INTEGRATED BACKUP BAND FOR USE IN FORMING AN ENCLOSURE FOR A MEDICAL DEVICE

(71) Applicant: NeuroPace, Inc., Mountain View, CA (US)

(72) Inventor: Joseph Vandenburg, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 115 days.

(21) Appl. No.: 15/492,979

(22) Filed: Apr. 20, 2017

(65) Prior Publication Data

US 2017/0216603 A1    Aug. 3, 2017

Related U.S. Application Data

(62) Division of application No. 14/329,525, filed on Jul. 11, 2014, now abandoned.

(51) Int. Cl.
| | |
|---|---|
| *A61N 1/375* | (2006.01) |
| *B23K 26/28* | (2014.01) |
| *B23K 26/24* | (2014.01) |
| *B23K 101/36* | (2006.01) |
| *B23K 101/12* | (2006.01) |
| *B23K 103/14* | (2006.01) |

(52) U.S. Cl.
CPC .............. *A61N 1/375* (2013.01); *B23K 26/24* (2013.01); *B23K 2101/125* (2018.08); *B23K 2101/36* (2018.08); *B23K 2103/14* (2018.08)

(58) Field of Classification Search
CPC ........ A61N 1/375; B23K 26/28; B23K 26/24; B23K 2201/125; B23K 2201/36; B23K 2203/14
USPC .......................................................... 607/36
See application file for complete search history.

(56) References Cited

U.S. PATENT DOCUMENTS

| | | | | |
|---|---|---|---|---|
| 5,456,698 | A  * | 10/1995 | Byland | A61N 1/375 607/36 |
| 5,957,956 | A  * | 9/1999 | Kroll | A61N 1/375 607/5 |
| 2003/0017372 | A1 | 1/2003 | Probst et al. | |
| 2003/0040779 | A1* | 2/2003 | Engmark | A61N 1/375 607/36 |
| 2003/0171784 | A1 | 9/2003 | Dodd et al. | |
| 2003/0204216 | A1* | 10/2003 | Ries | A61N 1/375 607/36 |
| 2006/0178708 | A1* | 8/2006 | Rorvick | A61N 1/375 607/36 |

(Continued)

*Primary Examiner* — Carl H Layno
*Assistant Examiner* — Erin M Piateski
(74) *Attorney, Agent, or Firm* — Loza & Loza, LLP; David S. Sarisky

(57) ABSTRACT

An implantable medical device includes an enclosure having a sidewall and a welded seam in the sidewall, the seam extends along a perimeter of the enclosure. A thermoform is located adjacent a surface of the enclosure and is secured in place within the enclosure. A metalized surface is located adjacent an interior surface of the enclosure sidewall and is secured in place by the thermoform. The metalized surface extends along a perimeter of the enclosure and is configured to obstruct laser energy during a weld seam process. The metalized surface may be provided as a separate backup band component or may be integrated in a perimeter sidewall of the thermoform.

10 Claims, 13 Drawing Sheets

(56) References Cited

U.S. PATENT DOCUMENTS

2009/0018600 A1* 1/2009 Deininger ............... A61N 1/375
607/36
2009/0266573 A1* 10/2009 Engmark ............... A61N 1/375
174/50.54

* cited by examiner

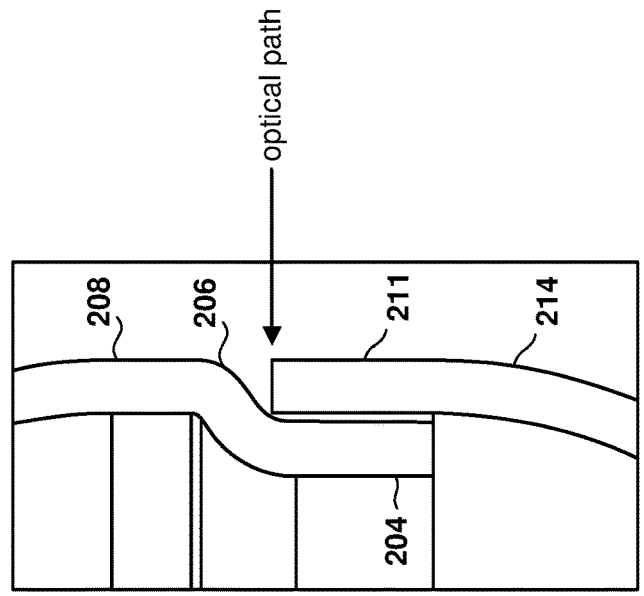
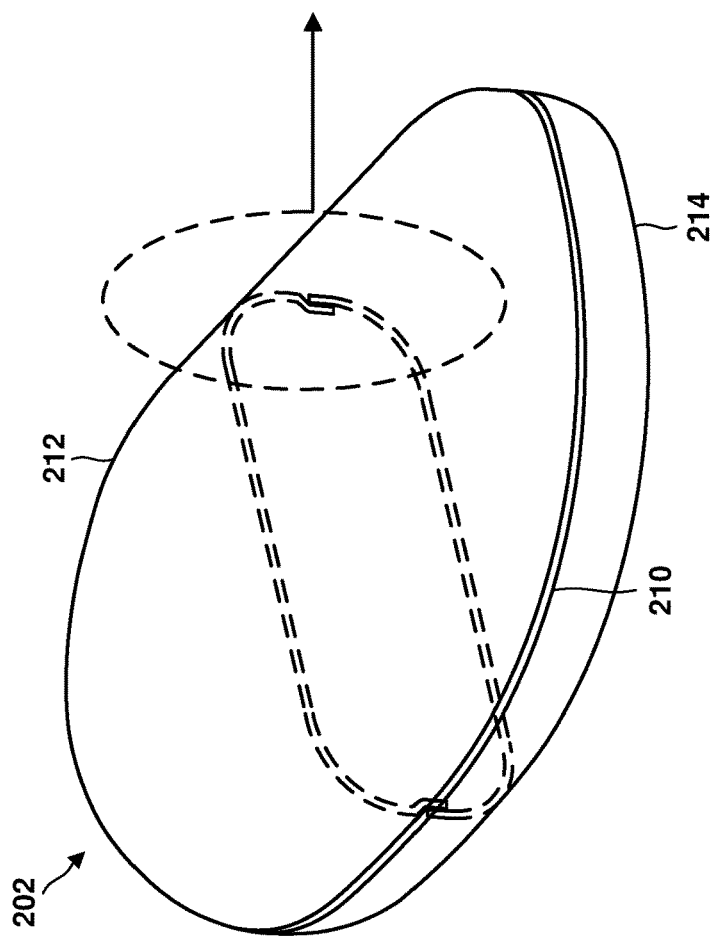
FIG. 2B
FIG. 2A

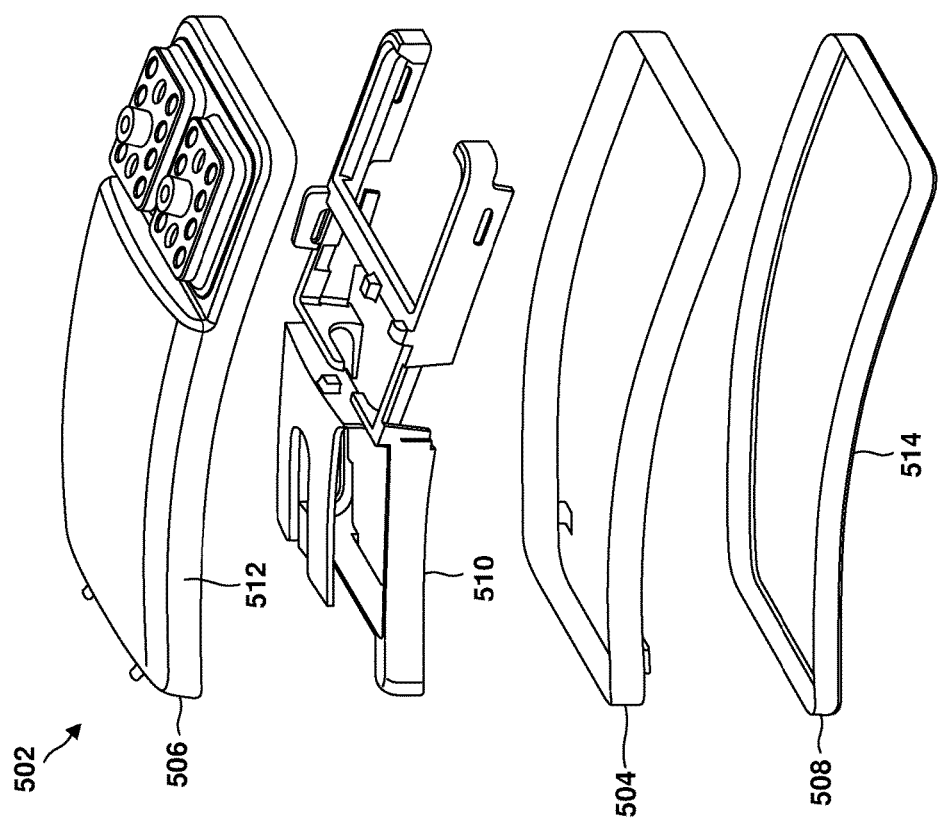

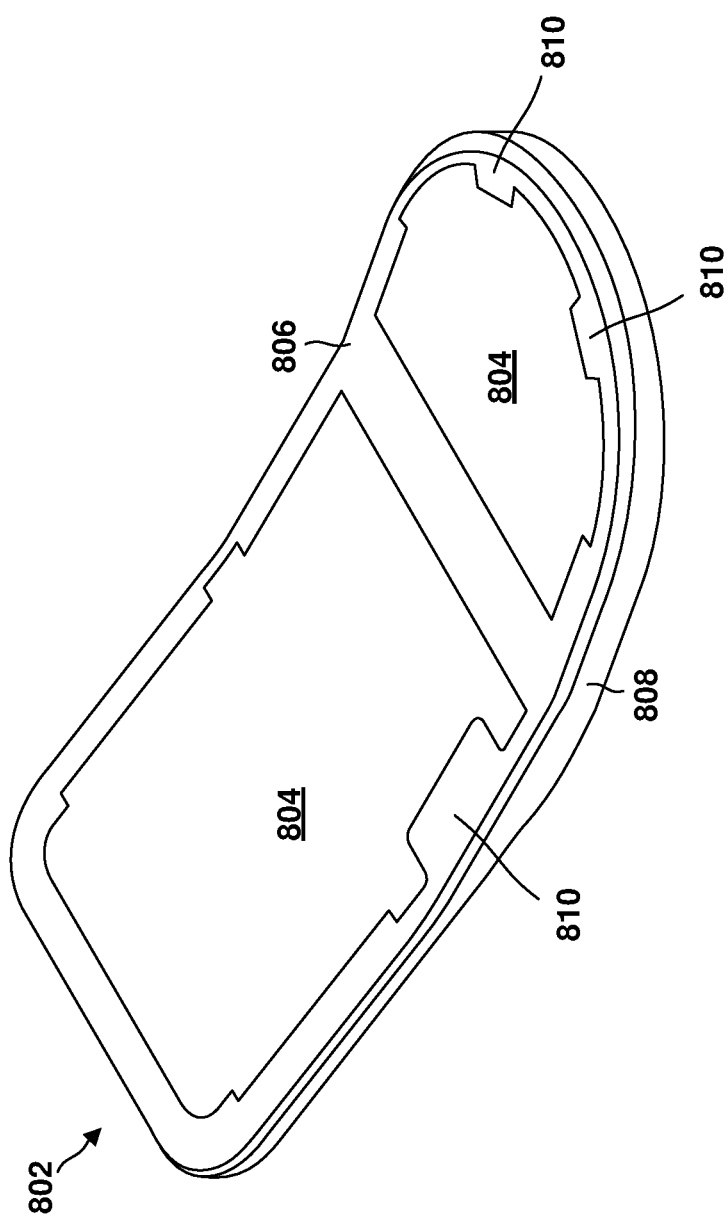

Step A

Step B

Step C

Step D

Step E

Step F

Step G

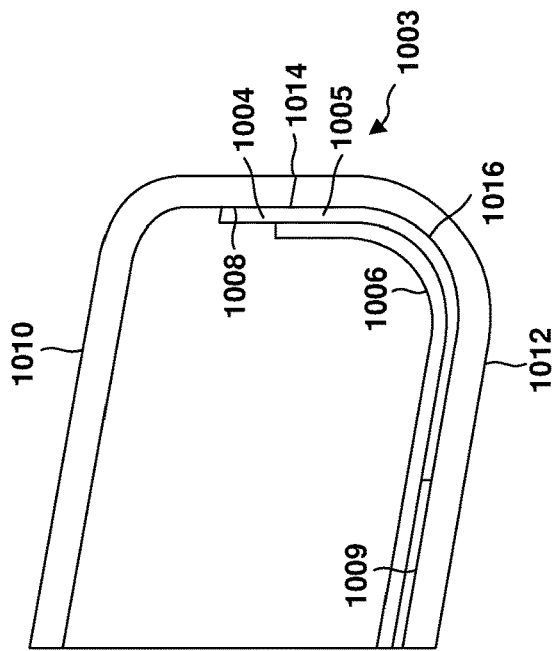
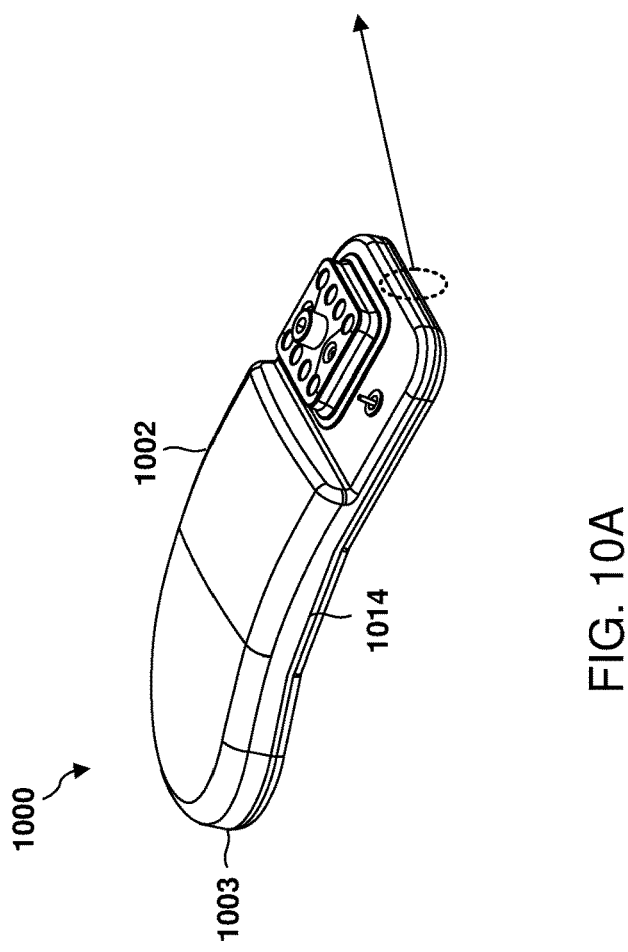
FIG. 10B
FIG. 10A

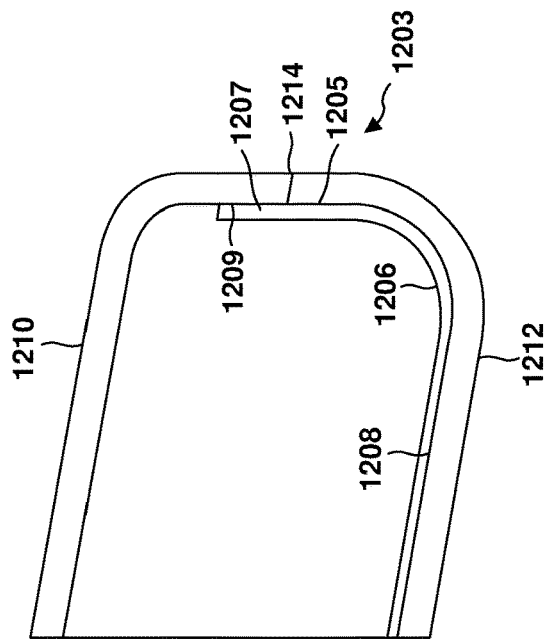
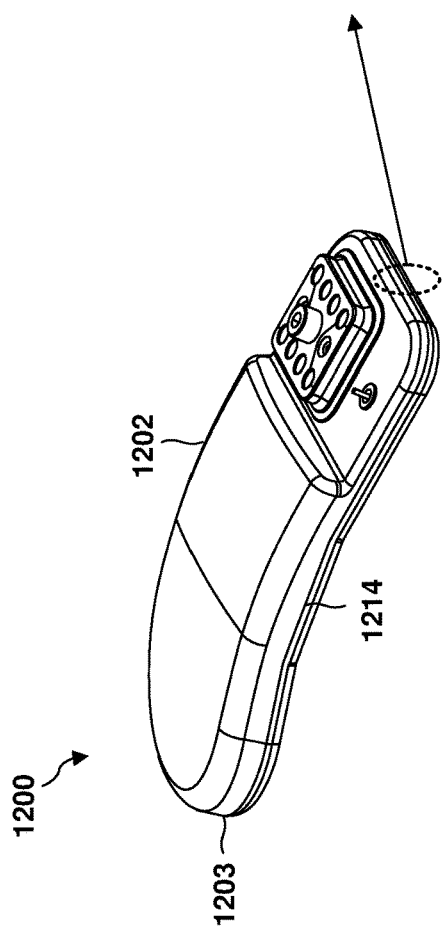
FIG. 12B
FIG. 12A

INTEGRATED BACKUP BAND FOR USE IN FORMING AN ENCLOSURE FOR A MEDICAL DEVICE

CROSS-REFERENCE TO RELATED APPLICATION

This application is a divisional of U.S. application Ser. No. 14/329,525, entitled "Integrated Backup Band For Use In Forming An Enclosure For A Medical Device," filed on Jul. 11, 2014, abandoned on Oct. 11, 2017, which is expressly incorporated by reference herein in its entirety.

BACKGROUND

Field

The present technology relates generally to enclosures for medical devices, and in particular, processes and components for sealing the enclosures.

Background

An enclosure for implantable medical devices may be configured from a pair of deep drawn titanium can halves that are laser welded together at a seam. An objective of the laser welded seam is to achieve a hermetic seal relative to the environment external to the device. Implantable medical devices are hermetically sealed to prevent the internal components from being damaged by moisture and to prevent injury to the patient that might be caused by the internal components.

Loss of hermeticity in an implanted medical device may result in a rapid increase of moisture within the device, resulting in an electrical short of internal components. An electrical short of internal components can result in one or more failure modes such as impaired device function, electrical shock of the implanted patient, or excessive heating of tissues in the implant area. Loss of hermeticity may also result in a material used inside the enclosure coming into unintended contact with patient tissue.

The laser welding process requires high density laser energy, sufficient to melt and fuse the titanium material of the top and bottom can halves. During the seam weld process, laser energy may pass through the seam between the abutting edges of each can half thereby presenting some risk to the internal components. For example, laser energy passing through the abutted edges of the top and bottom cans may vaporize internal components, e.g., plastic frames, which in turn, may result in a conductive residue further resulting in an electrical short of components. Laser energy passing through the abutted edges may also cause direct damage to temperature sensitive components such as the battery or soldered components on a printed circuit assembly. Damage to any of these components can result in a variety of failures ranging from impaired device function to serious injury or death to the patient.

Accordingly, to protect the internal components from being damaged during laser welding, a component is typically provided so that during laser welding, the component will obstruct the path of the laser beyond the desired location for the seam so that laser energy will not reach the internal components. The component also serves to capture molten metal, mitigating contact with internal components or a loose particulate within the device. The component used to provide the obstruction is sometimes referred to as a "backup band." Other terms such as "weld ring," or "weld band" are used to describe this type of component.

SUMMARY

An implantable medical device includes an enclosure having an interior surface, a sidewall, and a welded seam in the sidewall, where the seam extends along a perimeter of the enclosure. A metalized surface is located adjacent the interior surface of the enclosure and is secured in place by a thermoform. The metalized surface extends along a perimeter of the enclosure and is positioned behind the location of the seam, so that it will obstruct laser energy during a weld seam process. The metalized surface may be provided as a separate backup band component or may be integrated in a perimeter sidewall of the thermoform.

BRIEF DESCRIPTION OF THE DRAWINGS

The accompanying drawings, which are incorporated in and form a part of this specification, illustrate and serve to explain the principles of embodiments in conjunction with the description. Unless specifically noted, the drawings referred to in this description should be understood as not being drawn to scale.

FIG. 2A is a perspective view of a prior art enclosure for an implantable medical device formed from a top can half and a bottom can half.

FIG. 2B is a partial cross-section of the enclosure of FIG. 2A in the region identified by the dashed circle and illustrating the juncture of the top can half and the bottom can half.

FIG. 5 is a perspective, exploded view of some components of an implantable medical device according to embodiments, including a top can half, a frame, a backup band, and a bottom can half.

FIG. 8 is a perspective view of the thermoform of FIG. 6.

FIG. 10A is a perspective view of an implantable medical device provided with a backup band according to embodiments, after a seam between the top can half and the bottom can half has been laser welded.

FIG. 10B is a partial cross-section of the implantable medical device of FIG. 10A in the region identified by the dashed circle and illustrating a thermoform, the backup band, the top can half and the bottom can half.

FIG. 12A is a perspective view of an implantable medical device provided with a thermoform according to embodiments, wherein the thermoform has a metalized surface, after a seam between the top can half and the bottom can half has been laser welded.

FIG. 12B is a partial cross-section of the implantable medical device of FIG. 12A in the region identified by the dashed circle and illustrating the thermoform, the top can half and the bottom can half.

DETAILED DESCRIPTION

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure. It should be understood that any aspect of the disclosure disclosed herein may be embodied by one or more elements of a claim.

A medical device system may include implantable components including one or more electrode-bearing brain leads for delivering stimulation to (or for sensing field potentials from) neural tissue and an active implantable medical device configured to deliver stimulation signals through the electrodes and leads and/or to receive and process physiological signals sensed by the electrodes from the patient (e.g., EEG signals). The lead(s) may be connected to the neurostimulator at a lead connector associated with an enclosure or housing of the neurostimulator.

Medical device systems including a cranially-implanted component also are described in, for example, U.S. Pat. No. 6,016,449 to Fischell, et al. for "System for Treatment of Neurological Disorders", issued Jan. 18, 2000, U.S. Pat. No. 6,810,285 to Pless et al. for "Seizure Sensing and Detection Using An Implantable Device," issued Oct. 24, 2004, and U.S. Pat. No. 6,690,974 to Archer et al. for "Stimulation Signal Generator for an Implantable Device" issued Feb. 10, 2004. Each of the '449, '285 and '974 patents is hereby incorporated by reference in the entirety.

Figure 1:
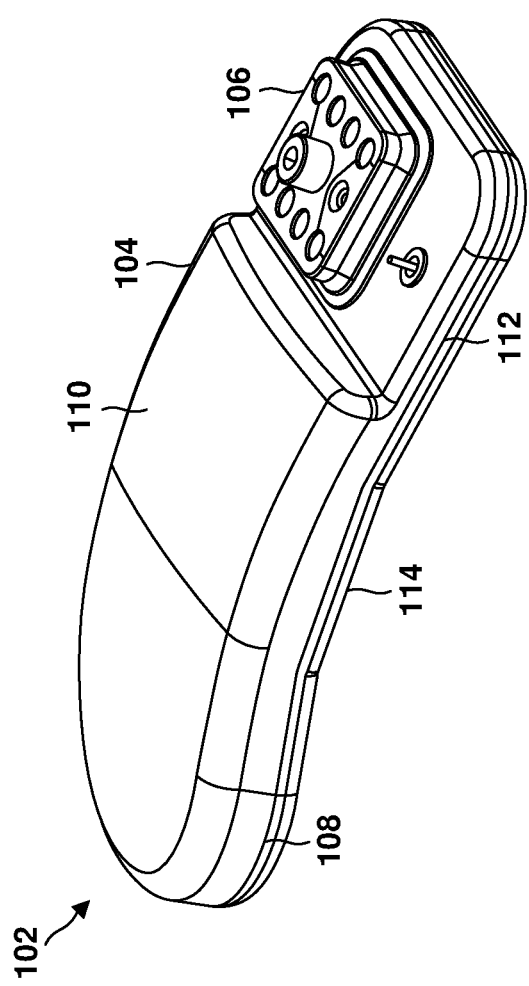
FIG. 1 is a perspective view of an implantable medical device including an enclosure formed from a top can half and a bottom can half and characterized by a seam joining the top can half to the bottom can half according to embodiments.

FIG. 1 is an illustration of an active implantable medical device 102. The device 102 includes an enclosure 104 and a feedthrough 106. Various elements (not shown), such as those which allow the device to carry out its functions, are housed within the enclosure 104. Such elements may include, for example, a battery, customized integrated circuits, a printed circuit assembly, an antenna for wireless communication, interconnects, and a frame. The feedthrough 106 provides an interface between the internal components and electrode-bearing leads. The medical device enclosure 104 is formed from two halves of metal, a top can half 110 and a bottom can half 114. Each half may be deep drawn from titanium.

The can halves are joined at an edge 108 of the top can half 110 and an edge 112 of the bottom can half 114. The enclosure is characterized by a slight curvature, such that neither of the edges 108, 112 are in a single plane. In the example device shown in FIG. 1, the curvature of the device approximates the curvature of a patient's cranium, as the device is intended to be implanted in a craniectomy formed in the patient's cranium.

As previously mentioned, enclosures for implantable medical devices are typically made of titanium can halves that are laser welded together to enclose the internal components and to achieve a hermetic seal relative to the environment external to the can. Several techniques have been used to protect the elements of the implantable medical device inside the enclosure from being exposed to energy from the laser when the top and bottom can halves are being sealed. These techniques are described with reference to FIGS. 2-5.

FIGS. 2A and 2B illustrate a medical device enclosure where one of the two can halves is configured to mate with the other can half so that a portion 204 of the top can half 212 overlaps with a portion 211 of the bottom can half 214. In FIGS. 2A and 2B, the top can half overlap portion 204 is configured to rest interiorly of the bottom can half portion 211. In this configuration, sometimes referred to as a "formed enclosure", a rim 206 is formed into a sidewall 208 of one of the can halves to allow the top and bottom can halves to overlap when assembled together. The seam is formed at the juxtaposition of the top can half 212 and the bottom can half 214, i.e., at the rim 206. When the laser energy is directed at the assembly to create the seam, the optical path of the laser will be obstructed by the metal portion 204 of the enclosure top can half 212 that overlaps with the bottom can half 214, thus preventing energy from the laser from reaching the interior of the enclosure.

Implantable device enclosures are almost exclusively designed with a planar or flat trim edge 210. In other words, the edges of the top and bottom can halves 212, 214 are in a single plane, and thus are relatively easy to mate together for laser welding a seam to achieve a hermetic seal. The formed enclosure configuration is only suitable for planar trim enclosures. The metal-forming operations that would be required to form a rim into a sidewall of the enclosure for a medical device enclosure that does not have a planar trim edge would be complicated or at the very least would be expensive to develop. Additionally, the medical device industry is designing smaller and thinner devices. Smaller formed enclosures introduce additional difficulty in forming the integrated backup band 204 feature into the sidewall of the enclosure.

Figure 3A:
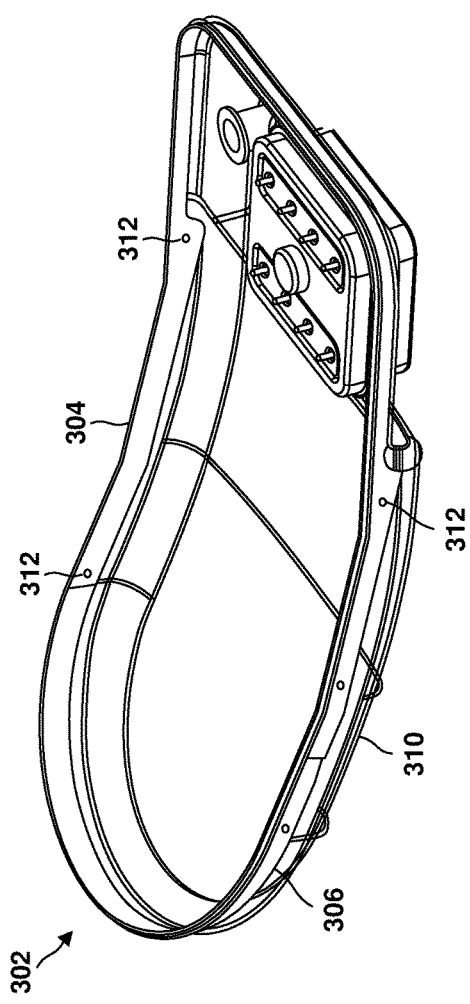
FIG. 3A is a perspective view of a bottom can half of an enclosure for an implantable medical device with a prior art backup band welded to the bottom can half.
Figure 3B:
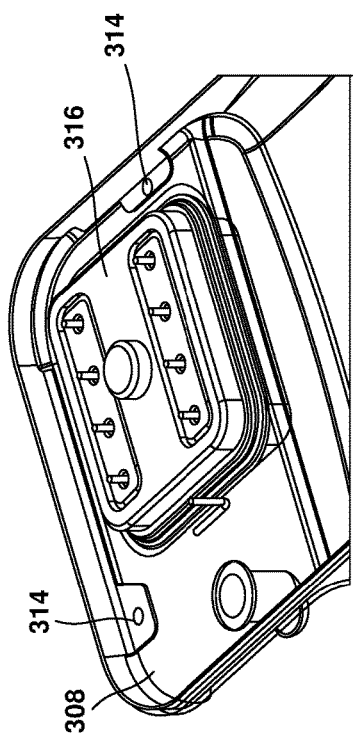
FIG. 3B is an enlarged detailed view of a portion of the bottom can half and welded backup band of FIG. 3A.

FIG. 3A and FIG. 3B illustrate a medical device enclosure assembly 302 with a welded backup band 304. The enclosure assembly 302 includes an enclosure component 310 and a feed-through 316. The enclosure component 310 may be a top can half or bottom can half of a medical device enclosure. In a welded backup band configuration, a separate backup band 304 component is secured to the enclosure component 310 by one or more weld spots. The backup band 304 may be welded to the can half at one or more weld spots 312, 314. The locations of the welds 312, 314 that secure the backup band 304 to the enclosure component 310 may include the side wall 306 of the enclosure component 310 and/or the surface 308 of the enclosure component adjacent to the sidewall of the enclosure.

The welded backup band configuration involves assembly operations that may result in increased chance of contamination and increased cost. With respect to contamination, for example, during handling and placement of the backup band 304 in the enclosure component 310, foreign particulate may become lodged between the backup band and the sidewall 306 or surface 308 of the enclosure component 310. Regarding cost, the process of welding the backup band 304 to the enclosure component 310 involves extra labor and material, thus leading to increase manufacturing cost.

Figure 4A:
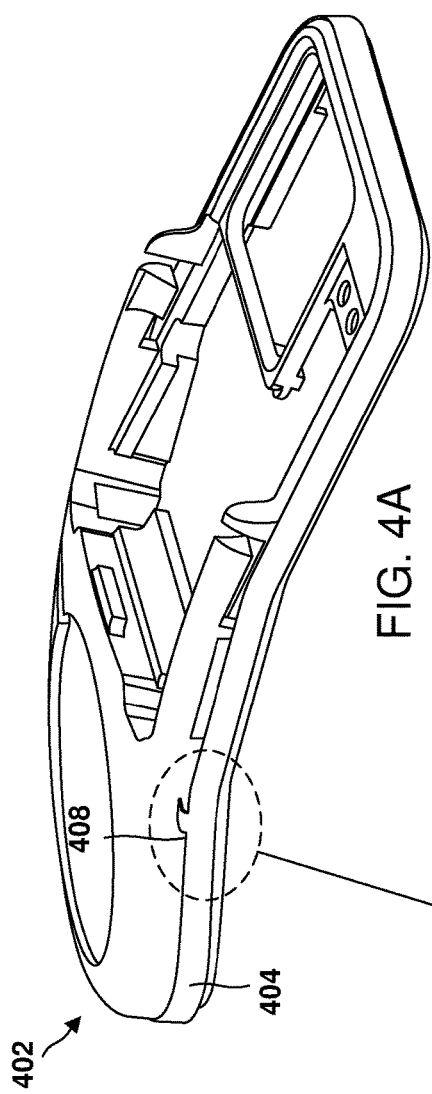
FIG. 4A is a perspective view of a prior art backup band integrated into a frame for components of an implantable medical device to be used inside the medical device enclosure.
Figure 4C:
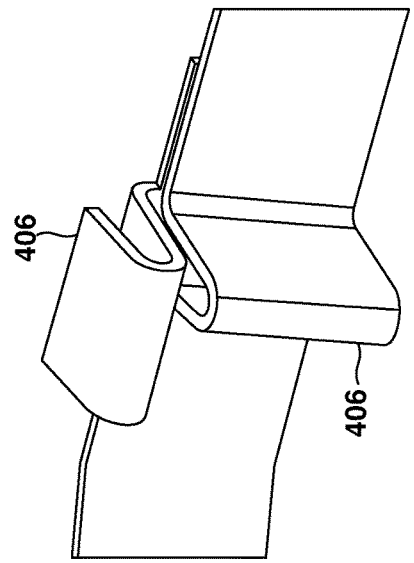
FIG. 4C is a further detailed view of the backup band of FIG. 4B.
Figure 4B:
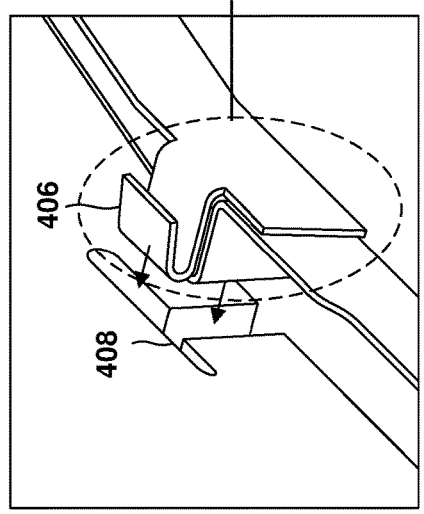
FIG. 4B is an exploded view of a portion of the frame and backup band of FIG. 4A in the region identified by the dashed circle.

FIG. 4A through FIG. 4C illustrate an internal component 402 of a medical device with an attached backup band 404. The internal component 402 may be a frame for holding other internal components. In an attached backup band design, features 406, 408 are designed into the backup band 404 and the internal component 402 respectively, to facilitate securing the band to the frame. With the attached backup band design, the band 404 is attached to the frame 402 as a subassembly and then subsequently placed into the device enclosure during assembly. The band 404 is located so as to provide protection of internal components from the seam weld laser energy.

The attached backup band configuration involves formation and assembly operations that may result in increased cost. For example, with respect to formation, the features 406, 408 included in the internal component 402 may require more complicated molding or additional cutting steps that increase the cost of the production of the internal component. Furthermore, the process of mechanically attaching the backup band 404 to the internal component 402 is complex and involves extra labor that adds to the overall manufacturing cost.

Embodiments disclosed below with reference to FIG. 5 and FIG. 6 include a backup band for incorporation into an implantable medical device having a non-planar form factor, and a method of assembling such an implantable medical device. The embodiments of FIG. 5 and FIG. 6 are advantageous over the backup band configurations of FIGS. 2-4 in that they avoid some of the manufacturing difficulties and increased costs associated with the formed enclosure configuration of FIG. 2, the welded backup band configuration of FIG. 3 and the attached backup band configuration of FIG. 4.

FIG. 5 illustrates components of a device 502 including a separate backup band 504. In this configuration, a backup band 504 is placed in the device 502 as a separate component, without being welded or mechanically attached to internal components. The device 502 is designed so that the backup band 504 is located at the seam between the top can half 506 and the bottom can half 508. In the separate component design, the band 504 is positioned in the proper location by the presence of the surrounding components. For example, the backup band 504 may be fixed between the internal frame 510 and the sidewalls 512, 514 of the top and bottom can halves. Once the cans 506, 508 are seam welded together, the band 504 is positioned with sufficient precision to protect internal components.

The separate component backup band configuration allows for backup band integration into a medical device without reliance on attachment features of other components or welding between the backup band and other components. The separate component backup band is applicable to medical devices having a thickness and form factor that accommodates loose placement of the backup band during the assembly process. This configuration may not be suitable for smaller devices. For example, the loose band configuration may not afford sufficient positional precision to be effective for smaller and thinner device designs. Other backup band configurations, such as described below with reference to FIGS. 6-10, may be more suitable for thinner devices having smaller form factors.

Figure 6:
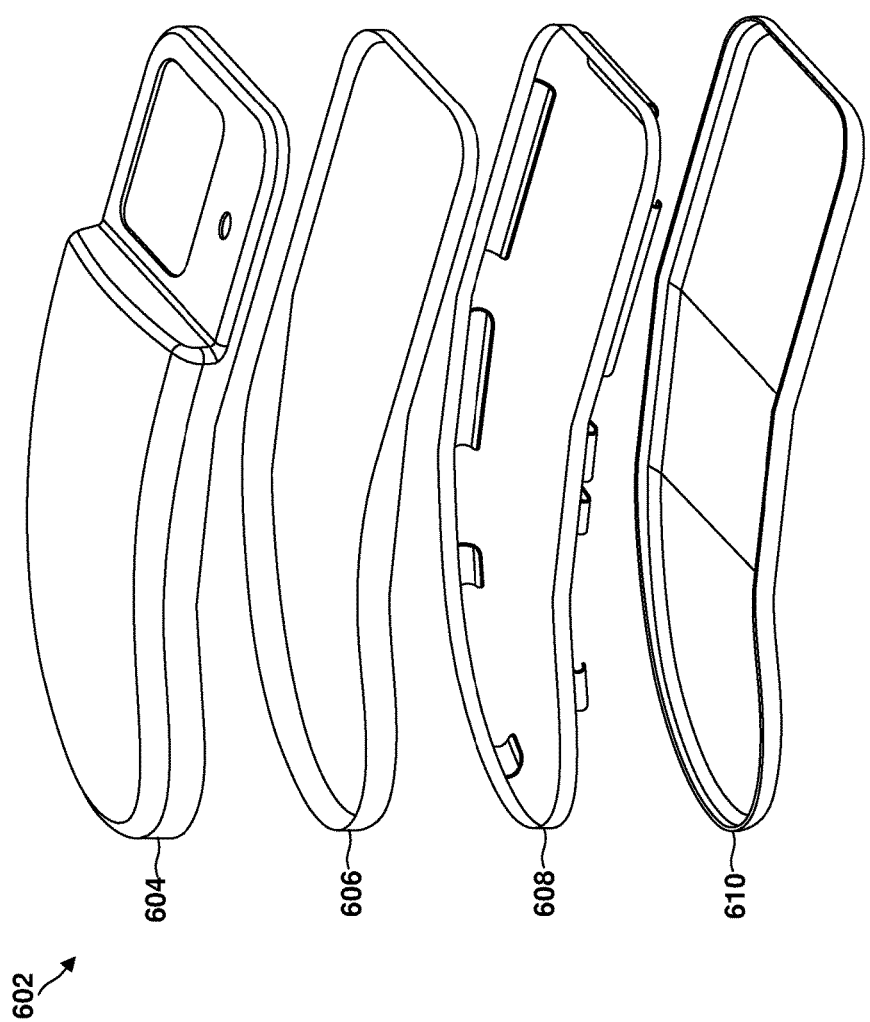
FIG. 6 is a perspective, exploded view of some of the components of an implantable medical device according to embodiments, including a top can half, a backup band, a thermoform layer, and a bottom can half.

FIG. 6 illustrates components of a non-planar device enclosure assembly 602. The components include a top can half 604, a thermoform 606, a backup band 608 and a bottom can half 610. This device enclosure assembly is suitable for medical devices having smaller form factors.

Figure 7:
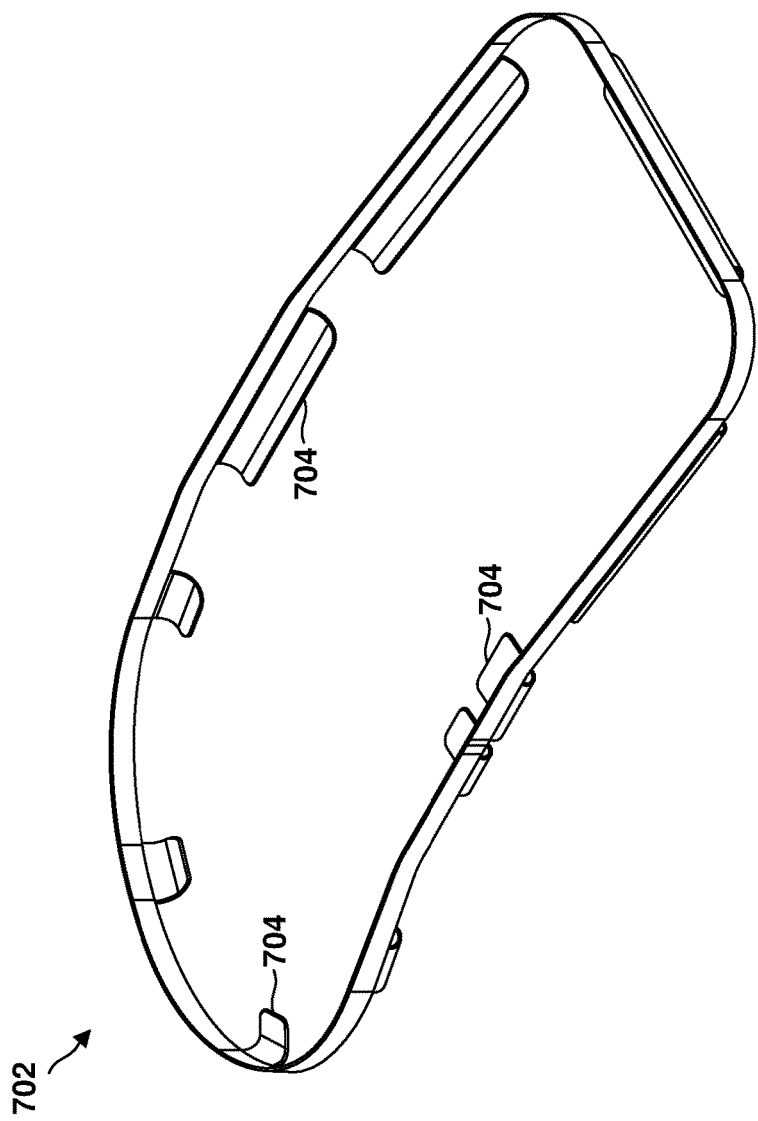
FIG. 7 is a perspective view the backup band of FIG. 6.

FIG. 7 illustrates the backup band of FIG. 6. The backup band 702 may be formed of a metal configured to obstruct the path of laser energy during a seam weld process. The size and shape of the backup band 702 is selected to match the size and shape of the interior of the medical device enclosure. In one configuration, the backup band 702 is formed from 0.005" thick titanium sheet. The backup band may also be formed of various grades of titanium alloy or nickel alloy with suitable metallurgical compatibility of the enclosure material. The backup band 702 includes a number of tabs 704 projecting inward toward the interior of the backup band. During assembly, the backup band 702 is fitted between one of the top can half or the bottom can half and a thermoform to thereby secure the backup band 702 in place. The tabs 704 are configured to abut an interior surface of the top or bottom can half to which the backup band is secured.

FIG. 8 illustrates the thermoform of FIG. 6. The thermoform 802 is a formed plastic film and includes a non-planar surface 806 and a perimeter side wall 808 extending around the non-planar surface. In one configuration, the thermoform 802 is made of electrically insulating film, between 0.002-0.010" thick. The thermoform functions to insulate electrically active internal components from the enclosure, thereby preventing damage to the device or harm to the patient in the event of an electrical short between electrically active components and the enclosure. The thermoform 802 also functions to secure the backup band in place during assembly. To that end, the thermoform 802 may be formed of a material rigid enough hold a separate backup band is place. For example, the thermoform 802 may be formed of a high temperature material such as a polyetherimide (PEI) (a.k.a. Ultem) or Polyether ether ketone (PEEK) have a modulus of elasticity in the range of 55-1740 kilopound per square inch (ksi).

The size and shape of the thermoform 802 closely matches the size and shape of the interior of a can half of the medical device enclosure while providing room to accommodate a backup band. The thermoform 802 may include one or more adhesive regions 804 formed of a layer of pressure sensitive adhesive. The pressure sensitive adhesive is configured to bond the thermoform 802 to an interior surface of a can half of the medical device enclosure. The pressure sensitive adhesive may include a cover-layer (not shown) to protect and preserve the adhesive prior to assembly. The cover-layer is configured to be removed from the adhesive regions 804 and discarded prior to assembly. In one configuration, the thermoform 802 may be configured to include one or more cutouts or notches 810 in one or more of the adhesive regions 804. The notches 810 correspond to regions where there is no adhesive. As evident from FIG. 9C below, these notches 810 generally align with the tabs 704 of the backup band 702. The absence of adhesive in the area of the tabs is beneficial in that it eliminates the thickness of the adhesive from the thickness of the assembly in the region of the tabs and overlying thermoform and thereby reduces the overall thickness of the assembly in these regions. In this configuration, the backup band is held in place by the portions of thermoform that overlaps the tabs. In another configuration, the thermoform 802 may be configured to include adhesive in the area of the tabs 704. This configuration provides an adhesive element, along with the overlapping thermoform element, to hold the backup band in place.

Figure 9A:
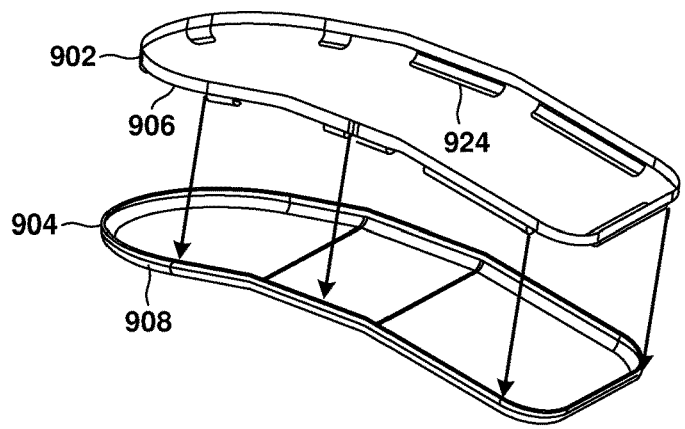
FIG. 9A through FIG. 9H are illustrations of a process of assembling a device that includes the enclosure of FIG. 1.

FIG. 9A through FIG. 9H illustrate an example process of assembling a device that includes the device enclosure of FIG. 1. The assembly process may employ tooling to assist an operator in positioning and holding components for assembly. The assembly process includes the following steps:

1. With reference to FIG. 9A, at step A, a backup band 902 is placed within the bottom can half 904 so the sidewall 906 of the backup band is positioned adjacent the sidewall 908 of the bottom can half. The backup band 902 is configured with sufficient rigidity to maintain an approximate position and shape within the bottom can half 904.

Figure 9B:
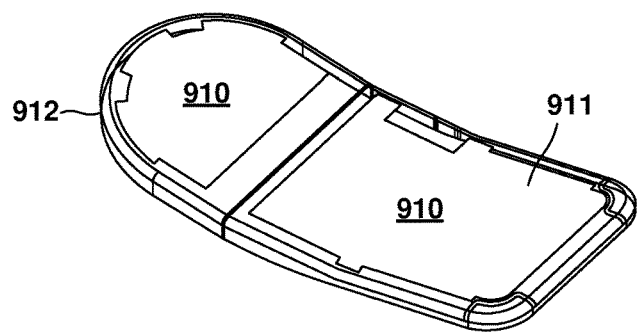

2. With reference to FIG. 9B, at step B, one or more cover layers 910 are removed from one or more regions of the non-planar surface 911 of a thermoform 912 to expose adhesive underneath the cover layers.

Figure 9C:
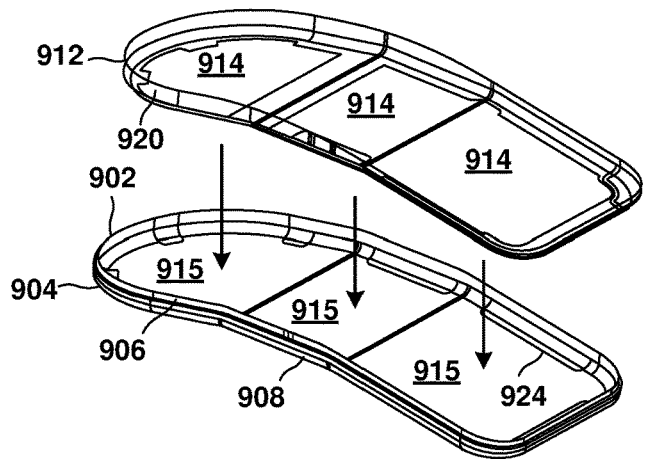

3. With reference to FIG. 9C, at step C, the thermoform 912, with exposed adhesive sections 914 facing downward, is positioned within the bottom can half 904. The adhesive sections 914 are positioned adjacent respective interior surfaces 915 of the bottom can half 904. The thermoform 912 is positioned so that the sidewall 906 of the backup band 902 is positioned between the sidewall 908 of the bottom can half 904 and the sidewall 920 of the thermoform. The thermoform 912 is also positioned so that the tabs 924 of the backup band 902 are positioned between the non-planar surface of the thermoform and the interior surfaces 915 of the bottom can half 904.

Figure 9D:
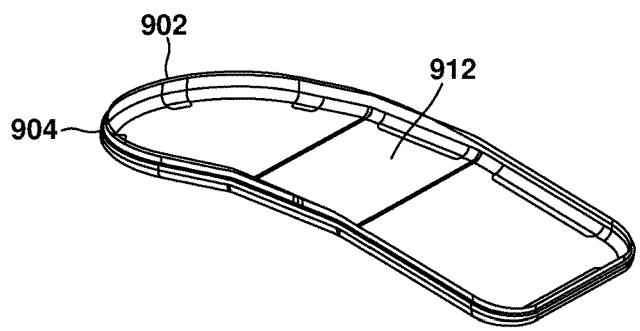

4. With reference to FIG. 9D, at step D, the thermoform 912 is pressed in place against the interior surfaces 915 (FIG. 9C) of the bottom can half 904. The pressure sensitive adhesive (not visible) on the thermoform 912 adheres to the interior surfaces 915 (FIG. 9C), thereby securing the thermoform and backup band 902 in place within the bottom can half 904.

In another configuration, the thermoform 912 may be designed to secure the backup band 902 directly to the thermoform. For example, the thermoform may have adhesive on the exterior of its side wall 920. In this case, the backup band 902 may be pressed against the adhesive and secured in place on the thermoform. The thermoform/backup band assembly may then be placed in the bottom can half 904 and secured in place by adhesive on the non-planar surface of the thermoform as described above. In another configuration, the adhesive layer of the thermoform 912 may be an optional design feature, depending on the device assembly process. For example, the thermoform 912 may be sized relative to the interior of the bottom can half 904 to provide a tight friction fit between the thermoform and the bottom can half sufficient to provide enough holding strength to retain the thermoform and backup band 902 in place during the remainder of the assembly process. Once the remainder of the device is assembled, internal components may hold the thermoform 912 and backup band 902 in place sufficiently for the seam weld process.

Figure 9E:
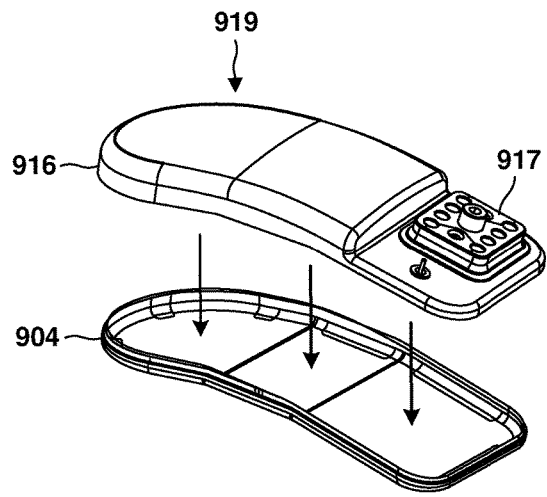
Figure 9F:
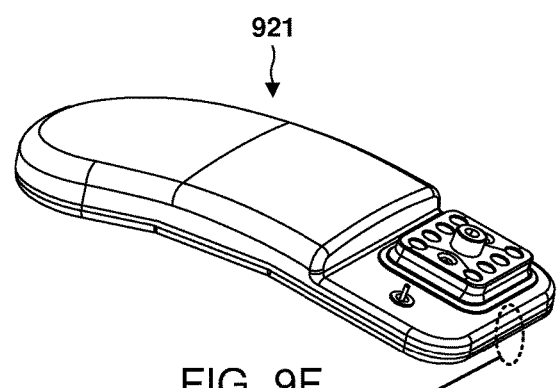

5. With reference to FIG. 9E and FIG. 9F, at step E, in a separate assembly process, device components including a feedthrough assembly 917 and other electronics (not visible) are assembled with respect to the top can half 916 to from a top can half 919 assembly. The top can half assembly 919 and the bottom can half 904 are then mated together to form an assembled device 921.

Figure 9G:
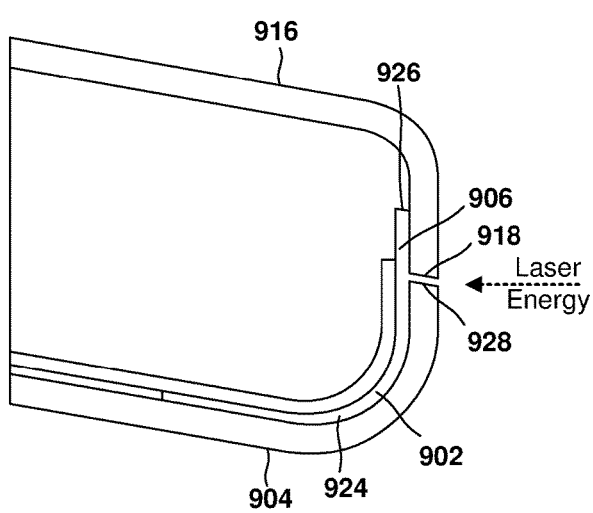

6. With reference to FIG. 9G, at step F, the top can half 916 and the bottom can half 904 are welded together at a gap 918 between the halves to form a weld seam around the perimeter of the device enclosure. The backup band 902 is in place to protect internal components during seam weld. The area of the cross-section illustrated of the assembled device illustrates the location of the backup band 902 across the gap 918 between the can halves 904, 916. This point of the cross-section also includes a tab 924 of the backup band 902. The gap 918 is illustrated to highlight a potential condition at the weld seam of an assembled device. If the backup band 902 were not present, laser energy could pass through the gap into the device and damage internal components (not illustrated). The presence of the sidewall 906 of the backup band 902 protects internal components by blocking laser energy and capturing potential weld splatter during the seam weld process.

Figure 9H:
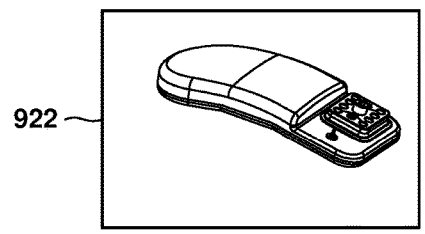

7. With reference to FIG. 9H, at step G, after completion of the seam weld process, a fine leak test is typically performed to verify the device is hermetic. The fine leak test is performed by placing the welded device within a vacuum chamber 922. In the presence of a vacuum the leak test equipment detects the presence of helium potentially leaking out from within the enclosure.

FIG. 10A and FIG. 10B are illustrations of an assembled implantable medical device 1000 having a non-planar enclosure 1002 with a metalized surface provided by a backup band 1004. The enclosure 1002 has a sidewall 1003 defining a perimeter of the enclosure and a welded seam 1014 in the sidewall that provides a hermetic seal around the enclosure. The sidewall 1003 is formed by portions of a top can half 1010 and a bottom can half 1012. The seam 1014 extends along the perimeter of the enclosure. A non-planar thermoform 1006 is located adjacent a surface 1009 of the bottom can half 1012 of the enclosure and is secured in place within the enclosure. The thermoform 1006 may be secured in place within the enclosure by adhesive or a friction fit. A metalized surface is located adjacent an interior surface 1008 of the enclosure sidewall 1003 and extends along the perimeter of the enclosure. The metalized surface extends above and below the seam 1014 and is secured in place by the thermoform 1006.

The metalized surface is provided by the backup band 1004 and is configured to obstruct laser energy. For example, the perimeter sidewall 1005 of the backup band 1004 adjacent the interior surface 1008 of the enclosure sidewall 1003 may include the metalized surface. In one configuration, the entire backup band 1004 is formed of a metal configured to obstruct laser energy. In another configuration, a layer of metal configured to obstruct laser energy is applied to the sidewall 1005 of the backup band 1004. The backup band 1004 may also include at least one extension or tab 1016 extending from the sidewall 1005. The extension 1016 is located between the thermoform 1006 and the surface 1009 of the bottom can half 1012 of the enclosure.

When the backup band 1004 is assembled between the surface 1009 of the bottom can half 1012 of the enclosure 1002 and the thermoform 1006, the backup band 1004 is fixed against the interior surface 1009 of the medical device enclosure, in a position suitable for retaining laser energy and potential weld splatter during the seam weld process.

The backup band 1004 also assists in the alignment of the top and bottom can halves 1010, 1012. If the backup band 1004 is not present at the seam 1014 between the top and bottom cans, the can halves may misalign during the seam weld process resulting in the increased potential for reduced weld penetration and increased likelihood of a loss of device hermeticity. The presence of the backup band 1004 around the entire perimeter of the enclosure 1002 serves to align the can halves in all directions around the entire perimeter of the enclosure.

Figure 11:
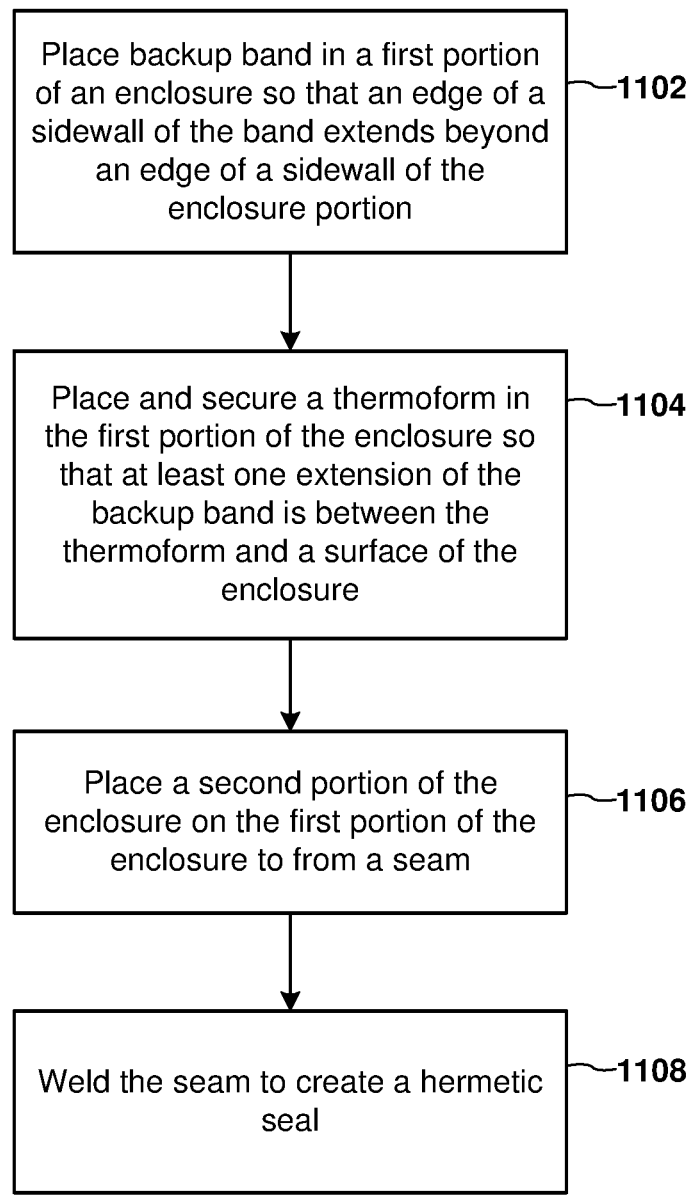
FIG. 11 is a flow chart of a general method of assembling an implantable medical device with a backup band.

FIG. 11 is a flow chart of a general method of assembling an implantable medical device with a backup band. At step 1102, a backup band 902 (FIG. 9A) is placed in a first portion of an enclosure 904. The back up band 902 has a perimeter sidewall 906 and at least one extension 924 extending from the sidewall. The backup band 902 is placed so that an edge 926 (FIG. 9G) of the sidewall 906 extends beyond an edge 928 of a sidewall of the first portion 904 of the enclosure.

At step 1104, a thermoform 912 (FIG. 9C) is placed and secured in the first portion of the enclosure 904 so that the at least one extension 924 of the backup band 902 is between the thermoform and a surface of the enclosure 904. At step 1106, a second portion of the enclosure 916 (FIG. 9E) is placed on the first portion of the enclosure 904 to form a seam 918 (FIG. 9G) between the first portion of the enclosure and the second portion of the enclosure. At step 1108, the seam 918 between the first portion of the enclosure 904 and the second portion of the enclosure 916 is welded to create a hermetic seal 1014 (FIG. 10B) along the seam 918.

In another configuration, the backup band is integrated into the thermoform. For example, the functionality of a backup band may be achieved by metalizing the exterior surface of the thermoform using techniques known in the art, such as physical vapor deposition. The metalized surface provides a reflective coating to reflect seam weld energy. A metalized thermoform may be fabricated from a high temperature material such as a polyetherimide (PEI) (a.k.a. Ultem) or Polyether ether ketone (PEEK) to withstand the small portions of laser energy present during the seam weld process.

It is understood that the specific order or hierarchy of steps in the method and flow chart is an illustration of exemplary approaches. Based upon design preferences, it is understood that the specific order or hierarchy of steps in the method and flow chart may be rearranged. Further, some steps may be combined or omitted. The accompanying method claims present elements of the various steps in a sample order, and are not meant to be limited to the specific order or hierarchy presented.

FIG. 12A and FIG. 12B are illustrations of an assembled implantable medical device 1200 having a non-planar enclosure 1202 with a metalized surface provided by a non-planar thermoform 1206. The enclosure 1202 has a sidewall 1203 defining a perimeter of the enclosure and a welded seam 1214 in the sidewall that provides a hermetic seal around the enclosure. The sidewall 1203 is formed by portions of a top can half 1210 and a bottom can half 1212. The seam 1214 extends along the perimeter of the enclosure. The thermoform 1206 is located adjacent a surface 1208 of the bottom can half 1212 of the enclosure and a surface 1209 of the top can half 1210. The thermoform 1206 may be secured in place within the enclosure by adhesive or a friction fit. An exterior sidewall 1207 of the thermoform 1206 is adjacent the interior surface 1205 of the enclosure sidewall 1203. A metalized surface is integrated with the exterior sidewall 1207. The metalized surface is thus located adjacent the interior surface 1205 of the enclosure sidewall 1203 and extends along the perimeter of the enclosure 1202. The metalized surface also extends above and below the seam 1214.

The backup band embodiments and assembly methods disclosed herein generally apply to any devices that require a process to join two halves of an enclosure. The embodiments provide an advantage over the current state of the art device enclosure designs by readily accommodating non-planar can trim geometry. A non-planar trim provides additional freedom to design curved devices to accommodate particular parts of the body such as the skull. The embodiments provide an advantage in the manufacturability of medical devices, by not requiring special processes or tooling to achieve the functionality of the backup band. The embodiments provide device design freedom by easily accommodating complex enclosure geometry. The embodiments limit component count by utilizing additional functionality of a thermoform. The thermoform positions and secures the backup band during device assembly and insulates electrically active internal components of a device from the device enclosure.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other devices having enclosures with a weld seam. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of assembling an implantable medical device, the method comprising: a) placing a backup band in a first half-enclosure having a surface and a sidewall extending from the surface, the backup band having a sidewall and comprising an edge, the backup band placed in the first half-enclosure so that a portion of the sidewall of the backup band comprising the edge extends beyond an edge of the sidewall of the first half-enclosure; b) after performing step a), placing a thermoform in the first half-enclosure, the thermoform having a surface and a sidewall extending from the surface, wherein the thermoform is placed so that the sidewall of the backup band is between the sidewall of the first half-enclosure and the sidewall of the thermoform; c) after performing step b), securing the backup band within the first half-enclosure by securing the thermoform to the first half-enclosure; d) placing a second half-enclosure relative to the first half-enclosure, the second half-enclosure having a surface and a sidewall extending from the surface, the first half-enclosure and the second half-enclosure placed relative to each other so that the sidewall of the second half-enclosure is adjacent to and surrounds the portion of the backup band that extends beyond the edge of the sidewall of the first half-enclosure, and the edge of the first half-enclosure and the edge of the second half-enclosure align with and abut each other to form a seam; and e) welding the seam to create a hermetic seal, wherein the backup band comprises at least one extension that extends inward from the sidewall of the backup band, and securing the backup band within the first half-enclosure by securing the thermoform to the first half-enclosure comprises placing the thermoform so that the at least one extension of the backup band is secured between the surface of the thermoform and the surface of the first half-enclosure.

2. The method of claim 1, wherein the backup band has no device components associated with it while it is being placed in the first half-enclosure.

3. The method of claim 1, wherein securing a thermoform to the first half-enclosure comprises:

exposing an adhesive on the surface of the thermoform prior to placing the thermoform in the first half-enclosure; and pressing the surface of the thermoform against the surface of the first half-enclosure.

4. The method of claim 1, wherein securing a thermoform to the first half-enclosure comprises:

establishing a friction fit between the thermoform and the first half-enclosure.

5. The method of claim 1, further comprising:

assembling device components in the second half-enclosure prior to performing step d).

6. The method of claim 1, wherein the surface of the first half-enclosure is non-planar.

7. The method of claim 1, wherein the surface of the second half-enclosure is non-planar.

8. The method of claim 1, wherein the surface of the thermoform is non-planar.

9. The method of claim 1, wherein the sidewall of the backup band extends beyond an edge of the sidewall of the first half-enclosure along the entirety of the sidewall of the first half-enclosure.

10. The method of claim 1, wherein the sidewall of the backup band forms a continuous loop.

* * * * *